United States Patent
Boyd

(10) Patent No.: US 7,799,833 B2
(45) Date of Patent: Sep. 21, 2010

(54) SYSTEM AND METHOD FOR THE PRETREATMENT OF THE ENDPLATES OF AN INTERVERTEBRAL DISC

(75) Inventor: Lawrence M. Boyd, Durham, NC (US)

(73) Assignee: Spine Wave, Inc., Shelton, CT (US)

( * ) Notice: Subject to any disclaimer, the term of this patent is extended or adjusted under 35 U.S.C. 154(b) by 1530 days.

(21) Appl. No.: 10/282,666

(22) Filed: Oct. 29, 2002

(65) Prior Publication Data

US 2003/0082169 A1     May 1, 2003

Related U.S. Application Data

(60) Provisional application No. 60/336,333, filed on Nov. 1, 2001, provisional application No. 60/336,002, filed on Nov. 1, 2001.

(51) Int. Cl.
*A01N 37/02* (2006.01)

(52) U.S. Cl. .................. 514/564; 514/561; 623/16.11; 623/17.11

(58) Field of Classification Search .......... None
See application file for complete search history.

(56) References Cited

U.S. PATENT DOCUMENTS

| | | |
|---|---|---|
| 4,132,746 A | 1/1979 | Urry et al. |
| 4,187,852 A | 2/1980 | Urry et al. |
| 4,474,851 A | 10/1984 | Urry |
| 4,500,700 A | 2/1985 | Urry |
| 4,589,882 A | 5/1986 | Urry |
| 4,736,738 A | 4/1988 | Lipovsek et al. |
| 4,783,523 A | 11/1988 | Urry et al. |
| 4,870,055 A | 9/1989 | Urry et al. |
| 4,898,962 A | 2/1990 | Chan et al. |
| 4,904,260 A | 2/1990 | Ray et al. |
| RE33,258 E * | 7/1990 | Onik et al. ............ 604/22 |
| 5,030,215 A | 7/1991 | Morse et al. |
| 5,064,430 A | 11/1991 | Urry |
| 5,219,328 A | 6/1993 | Morse et al. |
| 5,235,041 A | 8/1993 | Cappello et al. |
| 5,259,971 A | 11/1993 | Smith Morse et al. |

(Continued)

OTHER PUBLICATIONS

"Annulus Fibrosus" and "Lavage". Stedman's Medical Dictionary (Twenty-Second Edition). The Williams and Wilkins Company, 1972. p. 87 and 684.*

(Continued)

*Primary Examiner*—Allison M Ford
(74) *Attorney, Agent, or Firm*—Maginot, Moore & Beck, LLP

(57) ABSTRACT

A method for the pre-treatment of an intervertebral disc prior to the introduction of a disc prosthesis or implant includes removing at least a portion of the nucleus pulposus of the intervertebral disc to expose at least a portion of the endplate of an adjacent vertebra to the disc. A fluent treatment material is then injected into the disc space to come into contact with the portion of the endplate. The fluent treatment material is operable to prepare the portion of the endplate to accommodate a disc prosthesis, implant or graft subsequently introduced into the disc space. Different fluent treatment materials are provided that depend upon the condition of the vertebral endplates.

16 Claims, 4 Drawing Sheets

U.S. PATENT DOCUMENTS

| | | | |
|---|---|---|---|
| 5,318,524 | A | 6/1994 | Morse et al. |
| 5,556,429 | A | 9/1996 | Felt |
| 5,641,648 | A | 6/1997 | Ferrari et al. |
| 5,722,977 | A | 3/1998 | Wilhelmy |
| 5,723,588 | A | 3/1998 | Donofrio et al. |
| 5,760,004 | A | 6/1998 | Stedronsky |
| 5,770,697 | A | 6/1998 | Ferrari et al. |
| 5,773,249 | A | 6/1998 | Cappello et al. |
| 5,773,577 | A | 6/1998 | Cappello |
| 5,800,549 | A | 9/1998 | Bao et al. |
| 5,808,012 | A | 9/1998 | Donofrio et al. |
| 5,817,303 | A | 10/1998 | Stedronsky et al. |
| 5,830,713 | A | 11/1998 | Ferrari et al. |
| 5,874,500 | A | 2/1999 | Rhee et al. |
| 5,888,220 | A | 3/1999 | Felt et al. |
| 5,936,035 | A | 8/1999 | Rhee et al. |
| 5,962,648 | A | 10/1999 | Berg |
| 6,004,782 | A | 12/1999 | Daniell |
| 6,015,474 | A | 1/2000 | Stedronsky |
| 6,018,030 | A | 1/2000 | Ferrari et al. |
| 6,033,654 | A | 3/2000 | Stedronsky et al. |
| 6,048,346 | A | 4/2000 | Reiley et al. |
| 6,051,648 | A | 4/2000 | Rhee et al. |
| 6,110,484 | A | 8/2000 | Sierra |
| 6,111,165 | A | 8/2000 | Berg |
| 6,113,639 | A | 9/2000 | Ray et al. |
| 6,123,687 | A | 9/2000 | Simonyi et al. |
| 6,140,072 | A | 10/2000 | Ferrari et al. |
| 6,165,489 | A | 12/2000 | Berg et al. |
| 6,166,130 | A | 12/2000 | Rhee et al. |
| 6,184,348 | B1 | 2/2001 | Ferrari et al. |
| 6,187,048 | B1 | 2/2001 | Milner et al. |
| 6,224,630 | B1 | 5/2001 | Bao et al. |
| 6,245,107 | B1 | 6/2001 | Ferree |
| 6,248,131 | B1 | 6/2001 | Felt et al. |
| 6,258,872 | B1 | 7/2001 | Stedronsky |
| 6,277,394 | B1 | 8/2001 | Sierra |
| 6,306,177 | B1 | 10/2001 | Felt et al. |
| 6,312,725 | B1 | 11/2001 | Wallace et al. |
| 6,323,278 | B2 | 11/2001 | Rhee et al. |
| 6,344,488 | B1 | 2/2002 | Chenite et al. |
| 6,355,776 | B1 | 3/2002 | Ferrari et al. |
| 6,380,154 | B1 | 4/2002 | Cappello et al. |
| 6,395,007 | B1 | 5/2002 | Bhatnagar et al. |
| 6,402,750 | B1 | 6/2002 | Atkinson et al. |
| 6,413,742 | B1 | 7/2002 | Olsen et al. |
| 6,423,333 | B1 | 7/2002 | Stedronsky et al. |
| 6,425,919 | B1 | 7/2002 | Lambrecht |
| 6,428,576 | B1 | 8/2002 | Haldimann |
| 6,428,978 | B1 | 8/2002 | Olsen et al. |
| 6,440,138 | B1 | 8/2002 | Reiley et al. |
| 6,443,988 | B2 | 9/2002 | Felt et al. |
| 6,447,512 | B1 | 9/2002 | Landry et al. |
| 6,482,235 | B1 | 11/2002 | Lambrecht et al. |
| 6,500,205 | B1 | 12/2002 | Michelson |
| 6,508,839 | B1 | 1/2003 | Lambrecht et al. |
| 6,592,625 | B2 | 7/2003 | Cauthen |
| 6,595,998 | B2 | 7/2003 | Johnson et al. |
| 6,685,695 | B2 | 2/2004 | Ferree |
| 7,004,945 | B2 * | 2/2006 | Boyd et al. .............. 606/92 |
| 2002/0045942 | A1 | 4/2002 | Ham |
| 2002/0111688 | A1 | 8/2002 | Cauthen |
| 2002/0120337 | A1 | 8/2002 | Cauthen |
| 2002/0120347 | A1 * | 8/2002 | Boyer, II et al. ......... 623/23.63 |
| 2002/0123807 | A1 | 9/2002 | Cauthen, III |
| 2002/0128630 | A1 | 9/2002 | Ferree |
| 2002/0151980 | A1 | 10/2002 | Cauthen |
| 2002/0156531 | A1 | 10/2002 | Felt et al. |
| 2002/0189622 | A1 | 12/2002 | Cauthen, III et al. |
| 2003/0033017 | A1 | 2/2003 | Lotz et al. |
| 2003/0120345 | A1 | 6/2003 | Cauthen |
| 2006/0247600 | A1 | 11/2006 | Yeung et al. |

OTHER PUBLICATIONS

"Edetic Acid". The Merck Index (Eleventh Edition). Merck & Co., Inc. 1989. Monograph 3484 at p. 550.*

Baogan et al. "The Relationship Between Cartilage End-Plate Calcification and Disc Degeneration, an Experimental Study". Chinese Medical Journal, 2001; 114(3):308-312.*

Caplan, Arnold I. PhD, Mehrun Elyaderani MD, Yu Mochizuki MD, Shigeyuke Wakitani MD, and Victor M. Goldberg MD, "Overview Principles of Cartilage Repair and Regeneration: Principles of Cartilage Repair and Regeneration," Clinical Orthopaedics and Related Research, Voluem 342, Sep. 1997, Available online at http://gatewayl.ovid.com/ovidweb.cgi, (18 pages).

Grande, Daniel A. Phd, Arnold S. Breitbart MD, James Mason PhD, Carl Paulino MD, Jordon Laser BS, and Robert E. Schwartz MD, "Cartilage Tissue Engineering: Current Limitations and Solutions," Clinical Orthopaedics and Related Research, vol. 367S, Oct. 1999, Available online at http://gatewayl.ovid.com/ovidweb.cgi, (13 pages).

Toolan B. C., S. R. Frenkel, D. S. Pereira, and H. Alexander, "Development of a Novel Osteochondral Graft for Cartilage Repair," 1998, (6 pages).

Obradovic, B., I. Martin, R. F. Padera, S. Treppo, L. E. Freed, and G. Vunjak-Novakovic, "Integration of Engineered Cartilage," Journal of Orthopaedic Research, 2001, (9 pages).

Chen J., S. Maniwa, and M. Ochi, "Influence of trypsin on the biological bonding of cartilaginous surface to bone in rabbits," Clinical And Experimental Forum, 2000, (5 pages).

Roberts, Sally PhD, Jill P. G. Urban PhD, Helena Evans BSc, and Stephen M. Eisenstein PhD, "Transport Properties of the Human Cartilage Endplate in Relation to Its Composition and Calcification," Spine, vol. 21(4), Feb. 15, 1996, Available online at http://gatewayl.ovidcom/ovidweb.cgi, (11 pages).

Iwahashi, Masaki MD, Hiromi Matsuzaki MD, Yasuaki Tokuhashi MD, Ken Wakabayashi MD, and Yoshinao Uematsu MD, "Mechanism of Invertertebral Disc Degeneration Caused by Nicotine in Rabbits to Explicate Intervertebral Disc Disorders Caused by Smoking," Spine, vol. 27, No. 13, (6 pages), 2002.

Bernick, Sol PhD and Rene Cailliet MD, "Vertebral End-Plate Changes with Aging of Human Vertebrae," Spine, vol. 7, No. 2, 1982, (6 pages).

"Broad List of Proteases and Inhibitors," (3 pages).

* cited by examiner

SYSTEM AND METHOD FOR THE PRETREATMENT OF THE ENDPLATES OF AN INTERVERTEBRAL DISC

REFERENCE TO RELATED APPLICATIONS

This application claims priority to provisional application Ser. No. 60/336,002, entitled "Devices, Methods and Assemblies for Intervertebral Disc Repair and Regeneration", and provisional application Ser. No. 60/336,333, entitled "Pretreatment of Cartilaginous Endplates Prior to Treatment of the Intervertebral Disc with an Injectable Biomaterial", both of which were filed on Nov. 1, 2001, and the disclosure of which are both incorporated herein by reference.

BACKGROUND OF THE INVENTION

The present invention relates generally to the treatment of spinal diseases and injuries, and more specifically to the restoration of the spinal disc following the treatment. The invention contemplates devices and methods for restoring the normal intervertebral disc space height and for facilitating the introduction of biomaterials for use in the repair and restoration of the intervertebral disc.

The intervertebral disc is divided into two distinct regions: the nucleus pulposus and the annulus fibrosus. The nucleus lies at the center of the disc and is surrounded and contained by the annulus. The annulus contains collagen fibers that form concentric lamellae that surround the nucleus and insert into the endplates of the adjacent vertebral bodies to form a reinforced structure. Cartilaginous endplates are located at the interface between the disc and the adjacent vertebral bodies.

The intervertebral disc is the largest avascular structure in the body. The cells of the disc receive nutrients and expel waste by diffusion through the adjacent vascularized endplates. The hygroscopic nature of the proteoglycan matrix secreted by cells of the nucleus operates to generate high intra-nuclear pressure. As the water content in the disc increases, the intra-nuclear pressure increases and the nucleus swells to increase the height of the disc. This swelling places the fibers of the annulus in tension. A normal disc has a height of about 10-15 mm.

There are many causes of disruption or degeneration of the intervertebral disc that can be generally categorized as mechanical, genetic and biochemical. Mechanical damage includes herniation in which a portion of the nucleus pulposus projects through a fissure or tear in the annulus fibrosus. Genetic and biochemical causes can result in changes in the extracellular matrix pattern of the disc and a decrease in biosynthesis of extracellular matrix components by the cells of the disc. Degeneration is a progressive process that usually begins with a decrease in the ability of the extracellular matrix in the central nucleus pulposus to bind water due to reduced proteoglycan content. With a loss of water content, the nucleus becomes desiccated resulting in a decrease in internal disc hydraulic pressure, and ultimately to a loss of disc height. This loss of disc height can cause the annulus to buckle with non-tensile loading and the annular lamellae to delaminate, resulting in annular fissures. Herniation may then occur as rupture leads to protrusion of the nucleus.

Proper disc height is necessary to ensure proper functionality of the intervertebral disc and spinal column. The disc serves several functions, although its primary function is to facilitate mobility of the spine. In addition, the disc provides for load bearing, load transfer and shock absorption between vertebral levels. The weight of the person generates a compressive load on the discs, but this load is not uniform during typical bending movements. During forward flexion, the posterior annular fibers are stretched while the anterior fibers are compressed. In addition, a translocation of the nucleus occurs as the center of gravity of the nucleus shifts away from the center and towards the extended side.

Changes in disc height can have both local and global effects. On the local (or cellular, level) decreased disc height results in increased pressure in the nucleus, which can lead to a decrease in cell matrix synthesis and an increase in cell necrosis and apoptosis. In addition, increases in intra-discal pressure create an unfavorable environment for fluid transfer into the disc, which can cause a further decrease in disc height.

Decreased disc height also results in significant changes in the global mechanical stability of the spine. With decreasing height of the disc, the facet joints bear increasing loads and may undergo hypertrophy and degeneration, and may even act as a source of pain over time. Decreased stiffness of the spinal column and increased range of motion resulting from loss of disc height can lead to further instability of the spine, as well as back pain. The outer annulus fibrosus is designed to provide stability under tensile loading, and a well-hydrated nucleus maintains sufficient disc height to keep the annulus fibers properly tensioned. With decreases in disc height, the annular fibers are no longer able to provide the same degree of stability, resulting in abnormal joint motion. This excessive motion can manifest itself in abnormal muscle, ligament and tendon loading, which can ultimately be a source of back pain.

Radicular pain may result from a decrease in foraminal volume caused by decreased disc height. Specifically, as disc height decreases, the volume of the foraminal canal, through which the spinal nerve roots pass, decreases. This decrease may lead to spinal nerve impingement, with associated radiating pain and dysfunction.

Finally, adjacent segment loading increases as the disc height decreases at a given level. The discs that must bear additional loading are now susceptible to accelerated degeneration and compromise, which may eventually propagate along the destabilized spinal column.

In spite of all of these detriments that accompany decreases in disc height, where the change in disc height is gradual many of the ill effects may be "tolerable" to the spine and may allow time for the spinal system to adapt to the gradual changes. However, the sudden decrease in disc volume caused by the surgical removal of the disc or disc nucleus may heighten the local and global problems noted above. Many disc defects are treated through a surgical procedure, such as a discectomy in which the nucleus pulposus material is removed. During a total discectomy, a substantial amount (and usually all) of the volume of the nucleus pulposus is removed and immediate loss of disc height and volume can result. Even with a partial discectomy, loss of disc height can ensue. Discectomy alone is the most common spinal surgical treatment, frequently used to treat radicular pain resulting from nerve impingement by disc bulge or disc fragments contacting the spinal neural structures.

In another common spinal procedure, the discectomy may be followed by an implant procedure in which a prosthesis is introduced into the cavity left in the disc space when the nucleus material is removed. Thus far, the most prominent prosthesis is a mechanical device or a "cage" that is sized to restore the proper disc height and is configured for fixation between adjacent vertebrae. These mechanical solutions take on a variety of forms, including solid kidney-shaped implants, hollow blocks filled with bone growth material, push-in implants and threaded cylindrical cages.

In more recent years, injectable biomaterials have been more widely considered as an augment to a discectomy. As early as 1962, Alf Nachemson suggested the injection of room temperature vulcanizing silicone into a degenerated disc using an ordinary syringe. In 1974, Lemaire and others reported on the clinical experience of Schulman with an in situ polymerizable disc prosthesis. Since then, many injectable biomaterials or scaffolds have been developed as a substitute for the disc nucleus pulposus, such as hyaluronic acid, fibrin glue, alginate, elastin-like polypeptides, collagen type I gel and others. A number of patents have issued concerning various injectable biomaterials including: cross-linkable silk elastin copolymer discussed in U.S. Pat. No. 6,423,333 (Stedronsky et al.); U.S. Pat. No. 6,380,154 (Capello et al.); U.S. Pat. No. 6,355,776 (Ferrari et al.); U.S. Pat. No. 6,258, 872 (Stedronsky et al.); U.S. Pat. No. 6,184,348 (Ferrari et al.); U.S. Pat. No. 6,140,072 (Ferrari et al.); U.S. Pat. No. 6,033,654 (Stedronsky et al.); U.S. Pat. No. 6,018,030 (Ferrari et al.); U.S. Pat. No. 6,015,474 (Stedronsky); U.S. Pat. No. 5,830,713 (Ferrari et al.); U.S. Pat. No. 5,817,303 (Stedronsky et al.); U.S. Pat. No. 5,808,012 (Donofrio et al.); U.S. Pat. No. 5,773,577 (Capello); U.S. Pat. No. 5,773,249 (Capello et al.); U.S. Pat. No. 5,770,697 (Ferrari et al.); U.S. Pat. No. 5,760,004 (Stedronsky); U.S. Pat. No. 5,723,588 (Donofrio); U.S. Pat. No. 5,641,648 (Ferrari); and U.S. Pat. No. 5,235,041 (Capello et al.); protein hydrogel described in U.S. Pat. No. 5,318,524 (Morse et al.); U.S. Pat. No. 5,259, 971 (Morse et al.): U.S. Pat. No. 5,219,328 (Morse et al.); and U.S. Pat. No. 5,030,215; polyurethane-filled balloons discussed in 60/004,710 (Felt et al.); U.S. Pat. No. 6,306,177 (Felt et al.); U.S. Pat. No. 6,248,131 (Felt et al.) and U.S. Pat. No. 6,224,630 (Bao et al.); collagen-PEG set forth in U.S. Pat. No. 6,428,978 (Olsen et al.); U.S. Pat. No. 6,413,742 (Olsen et al.); U.S. Pat. No. 6,323,278 (Rhee et al.); U.S. Pat. No. 6,312,725 (Wallace et al.); U.S. Pat. No. 6,277,394 (Sierra); U.S. Pat. No. 6,166,130 (Rhee et al.); U.S. Pat. No. 6,165,489 (Berg et al.); U.S. Pat. No. 6,123,687 (Simonyi et al.); U.S. Pat. No. 6,111,165 (Berg); U.S. Pat. No. 6,110,484 (Sierra); U.S. Pat. No. 6,096,309 (Prior et al.); U.S. Pat. No. 6,051,648 (Rhee et al.); U.S. Pat. No. 5,997,811 (Esposito et al.); U.S. Pat. No. 5,962,648 (Berg); U.S. Pat. No. 5,936,035 (Rhee et al.); and U.S. Pat. No. 5,874,500 (Rhee et al.); chitosan in U.S. Pat. No. 6,344,488 to Chenite et al.; a variety of polymers discussed in U.S. Pat. No. 6,187,048 (Milner et al.; recombinant biomaterials in 60/038,150 (Urry); U.S. Pat. No. 6,004,782 (Daniell et al.); U.S. Pat. No. 5,064,430 (Urry); U.S. Pat. No. 4,898,962 (Urry); U.S. Pat. No. 4,870,055 (Urry); U.S. Pat. No. 4,783,523 (Urry et al.); U.S. Pat. No. 4,783,523 (Urry et al.); U.S. Pat. No. 4,589,882 (Urry); U.S. Pat. No. 4,500,700 (Urry); U.S. Pat. No. 4,474,851 (Urry); U.S. Pat. No. 4,187,852 (Urry et al.); and U.S. Pat. No. 4,132, 746 (Urry et al.); and annulus repair materials described in U.S. Pat. No. 6,428,576 to Haldimann.

These references disclose biomaterials or injectable scaffolds that have one or more properties that are important to disc replacement, including strong mechanical strength, promotion of tissue formation, biodegradability, biocompatibility, sterilizability, minimal curing or setting time, optimum curing temperature, and low viscosity for easy introduction into the disc space. The scaffold must exhibit the necessary mechanical properties as well as provide physical support. It is also important that the scaffold be able to withstand the large number of loading cycles experienced by the spine. The biocompatibility of the material is of utmost importance. Neither the initial material nor any of its degradation products should elicit an unresolved immune or toxicological response, demonstrate immunogenicity, or express cytoxicity.

Generally, the above-mentioned biomaterials are injected as viscous fluids and then cured in situ. Curing methods include thermosensitive cross-linking, photopolymerization, or the addition of a solidifying or cross-linking agent. The setting time of the material is important—it should be long enough to allow for accurate placement of the biomaterial during the procedure yet should be short enough so as not to prolong the length of the surgical procedure. If the material experiences a temperature change while hardening, the increase in temperature should be small and the heat generated should not damage the surrounding tissue. The viscosity or fluidity of the material should balance the need for the substance to remain at the site of its introduction into the disc, with the ability of the surgeon to manipulate its placement, and with the need to assure complete filling of the intradiscal space or voids.

Since the intervertebral disc is an avascular structure, it relies upon the vascularized adjacent vertebral bodies to receive nutrients and expel waste. This fluid flow occurs by diffusion through the vertebral endplates. Thus, as shown in FIG. 1, a spinal disc D is disposed between adjacent vertebrae $V_1$ and $V_2$. The disc includes the annulus fibrosus A, which surrounds and contains the nucleus pulposus N. The portion of the adjacent vertebrae in contact with the nucleus constitutes the endplates $E_1$ and $E_2$.

As depicted in the figure, the bony vertebral bodies $V_1$ and $V_2$ are vascularized, as represented by the blood vessels B. The vertebral bodies are porous so fluid can pass to and from the vessels B. In particular, fluids traverse the semi-permeable cartilaginous endplates $E_1$ and $E_2$ as represented by the arrows entering and leaving the nucleus N. Fluids entering the nucleus provide nutrients to the cells of the nucleus, while fluids expelled from the disc constitute cellular metabolic waste products. The nutrients are required for cell metabolism and manufacture of extracellular matrix (e.g., collagen, proteoglycans, etc.) by the cells of the disc. This extracellular matrix provides the structure needed to resist mechanical loads and maintain normal anatomical relationships between the adjacent vertebrae. The metabolic waste products must be removed to prevent their accumulation within the disc, which build-up can lead to conditions less favorable to cell proliferation or synthesis (e.g., altered pH). Water can also diffuse through the endplates to maintain a proper intra-discal pressure, which ultimately results in an appropriate disc height.

Disc degeneration (discussed above) can result from decreases in cell nutrition and declining disc cell viability may occur through a variety of mechanisms. One common mechanism involves decreased diffusion through the adjacent vertebral endplates $E_1$ and $E_2$. The endplates are cartilaginous and have a thickness ranging from 0.1 mm in the region over the nucleus N to 1.6 mm at the region of the annulus fibrosus A. The endplates are also vascularized via arterioles and venous invaginations. With many types of disc degeneration, the endplates can thicken or lose vascularization, becoming increasingly impermeable and sclerotic.

As the endplates become more impermeable, diffusion through the endplates decreases. This decreased diffusion can lead to decreased transfer of nutrients to the disc cells, lower pH, reduced oxygen tension and increased cell apoptosis (programmed cell death) and necrosis. Ultimately, the altered cellular viability leads to reduced matrix synthesis by the cells of the disc. Cells under decreased nutritional influx and waste byproduct outflow are unable to synthesize the matrix needed to maintain the specialized matrix of the nucleus pulposus and inner annulus fibrosus. This specialized matrix consists of collagen and proteoglycans capable of resisting the high compressive forces exerted on the disc. The negatively charged branching structures on the large and small proteoglycans bind large amounts of water and provide for the viscoelastic properties of the healthy disc. With decreases in proteoglycan content, the intervertebral disc becomes progressively desiccated, which ultimately leads to the loss in disc height and increased instability discussed above.

Extracellular matrix forms both adjacent to the cells and distributed between the cells. The matrix distributed widely between the cells provides the overall structure needed by the nucleus pulposus to resist mechanical loading. The matrix formed adjacent to the cells (the pericellular matrix) is important in shielding the individual cells from excessive loading that could trigger gene expression changes (e.g., decreased synthesis of mRNA for matrix proteins), and could ultimately lead to cell apoptosis and necrosis. Decreased matrix synthesis in the face of poor nutrition and increased matrix breakdown by proteases, activated by the changing pH and oxygen tension, lead to progressive degeneration of the disc and increased vulnerability to repetitive trauma.

Frequently, and perhaps typically, disc degeneration and/or herniation is preceded by degeneration of the vertebral endplates. Treatment of the disc degeneration can proceed as outlined above—i.e., a discectomy followed by the introduction of some form of scaffold into the intradiscal space. In some cases, the scaffold is a solid implant or spinal fusion that does not preserve any of the mechanical properties of the disc. In many spinal fusions, the endplate is reduced to "bleeding bone" by means of a rongeur or rasp to enhance the fixation of the fusion implant to the adjacent vertebrae. In other fusion procedures, portions of the adjacent vertebrae are removed to make room for the fusion implant. In these cases, viability of the endplates is relatively unimportant.

However, where the scaffold is of the type described above that seeks to restore normal disc function (at least as much as possible), patency of the endplates is of critical concern. If the disc has sclerotic or thickened endplates, no restorative scaffold will work in its intended way because no fluid diffusion is permitted. In other words, if the foundation is deficient, the entire treatment of the disc will fall short of its goal.

Placement of cells within a matrix (or migration of cells into a matrix) is destined to fail if these cells cannot receive adequate nutrients or cannot expel metabolic products. For tissue engineering of the disc to be a viable reparative and regenerative strategy, the diseased endplate must be addressed in addition to the diseased intervertebral disc.

SUMMARY OF THE INVENTION

The present invention contemplates a method and system for addressing the diseased vertebral endplates in anticipation of treatment for a degenerative or diseased intervertebral disc. One step of the method calls for removing at least a portion of the nucleus pulposus of the intervertebral disc to expose at least a portion of the endplate of an adjacent vertebra to the disc. The method then includes the step of injecting a fluent treatment material into the disc space to come into contact with the portion of the endplate. The fluent treatment material is operable to prepare the portion of the endplate to accommodate a disc prosthesis, implant or graft subsequently introduced into the disc space.

In one aspect of the invention, the fluent treatment material is retained within the disc space for an incubation period sufficient for substantially complete operation of the fluent treatment material on the portion of the endplate. The fluent treatment material and any byproducts of its operation of the fluent treatment material on the portion of the endplate can be removed by lavage and flushing.

In some embodiments, the step of injecting a fluent treatment material includes simultaneously maintaining the vertebrae adjacent to the disc in a distracted position. In specific embodiments, this step includes introducing a cannulated distractor into the disc, the distractor operable to distract the adjacent vertebrae. The distractor includes a lumen in communication with the disc space through which the fluent treatment material is injected.

Various fluent treatment materials are contemplated depending upon the condition of the vertebral endplates and the nature of the disease or defect of the endplates. For instance, the fluent treatment material can be a decalcifying agent that is operable to remove calcification on the endplates. The decalcifying agent can be an acid such as EDTA.

In other cases, the endplates suffer from poor vascularity so the pre-treatment fluent material is operable to improve the vascularity of the endplates. Thus, in certain embodiments, the fluent treatment material is a VEGF (vascular endothelial growth factor). In other embodiments, the material can be a gene therapy material operable to transfect cells for the expression of a pre-determined cytokine.

Other treatments of the invention operate to enhance the integration of an implant or prosthesis with the vertebral endplates. Such fluent treatment materials can include biomaterials capable of digesting or removing proteoglycans that are detrimental to this integration. Such a material can include hyaluronidase.

Cell migration between the endplates and the prosthetic material subsequently introduced into the disc space can also be of concern. Certain pre-treatment materials can improve the cell migration characteristics of the vertebral endplates. For instance, trypsin can affect proteoglycan structures that reduce cell migration through the endplates.

Preferably, the step of injecting a fluent treatment includes providing a substantially enclosed volume around the portion of the endplate to restrict exposure of endplate other than said portion to said fluent treatment. In other words, some portions of the endplate may be adequate and may not require a pretreatment. Thus, one aspect of the invention contemplates a device having a central body configured to be received within the disc space. The body defines a central lumen therethrough and a number of openings in communication with the lumen, with means at the proximal end of the device for fluidly connecting to a source of the fluent treatment material to be applied to the vertebral endplates adjacent the disc space.

The device can include at least two legs extending from the body and configured to contact a vertebral endplate. The legs are disposed on opposite sides of at least some of the number of openings to define an enclosed volume about the openings when the legs are in contact with a vertebral endplate. The legs can be rigid to provide distraction support, or can be in the form of a conformal seal. With either approach, the legs help contain the fluent treatment material about the affected portion of the intervertebral endplate, and help prevent contact between the fluent material and other portions of the endplate that may not require treatment.

It is one object of the invention to provide a method for pre-treating an intervertebral disc to enhance the ability of a subsequently introduced prosthesis, graft or implant to become integrated into the disc space. Another object is realized by features of the invention that provide specific treatments for specific conditions of the vertebral endplates that have resulted from disease or defects.

Other objects and certain benefits of the invention will become apparent from the following written description, taken together with the accompanying figures.

DESCRIPTION OF THE PREFERRED EMBODIMENTS

Figure 1:
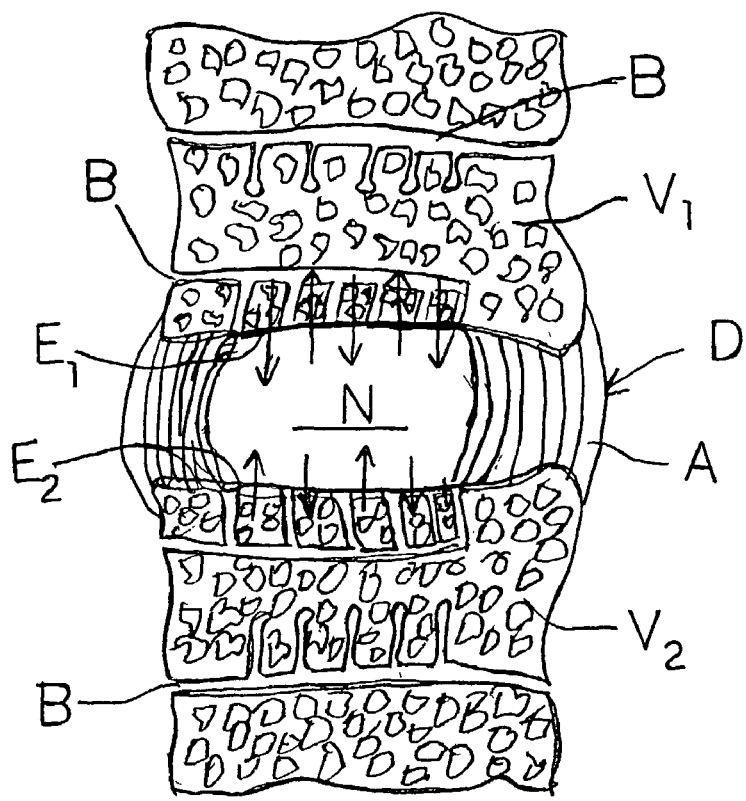
FIG. 1 is a lateral view of the spine illustrating the physical components of an intervertebral disc and adjacent vertebrae.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a procedure and device that is implemented following removal of a portion or substantially all of the natural nucleus pulposus of an intervertebral disc. This procedure may also involve removal of the inner annulus fibrosus, a structure known to primarily resist compressive loading. When disc material is removed, it is important to maintain the proper disc height during the introduction of a biomaterial that is intended to replace the removed nuclear material. Removal of disc material can be accomplished chemically, such as by the use of Chymopapain. However, the more common approach is by discectomy, which can be conducted as an open surgical procedure, via microscope-assisted visualization, or through percutaneous access.

Figure 2:
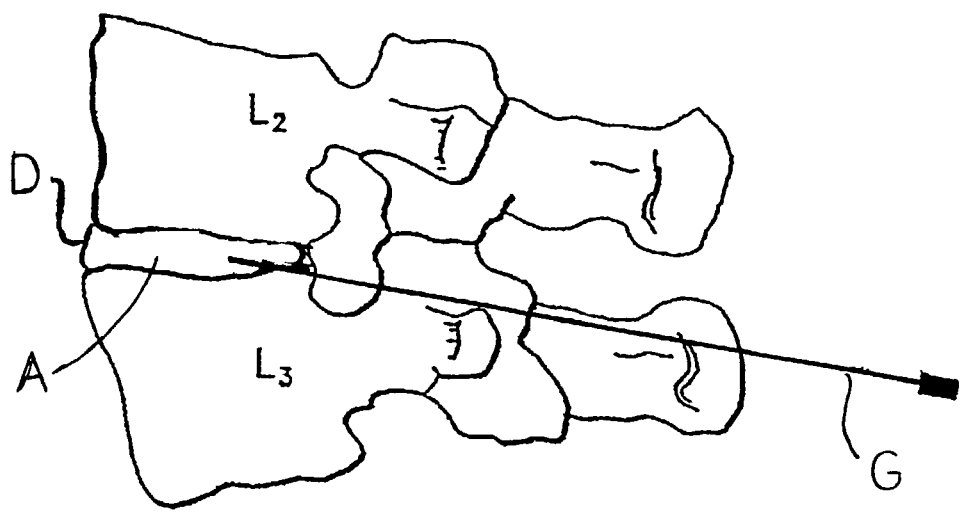
FIG. 2 is a lateral view a disc and adjacent vertebrae with a guide wire placed in accordance with one aspect of the present invention.
Figure 3:
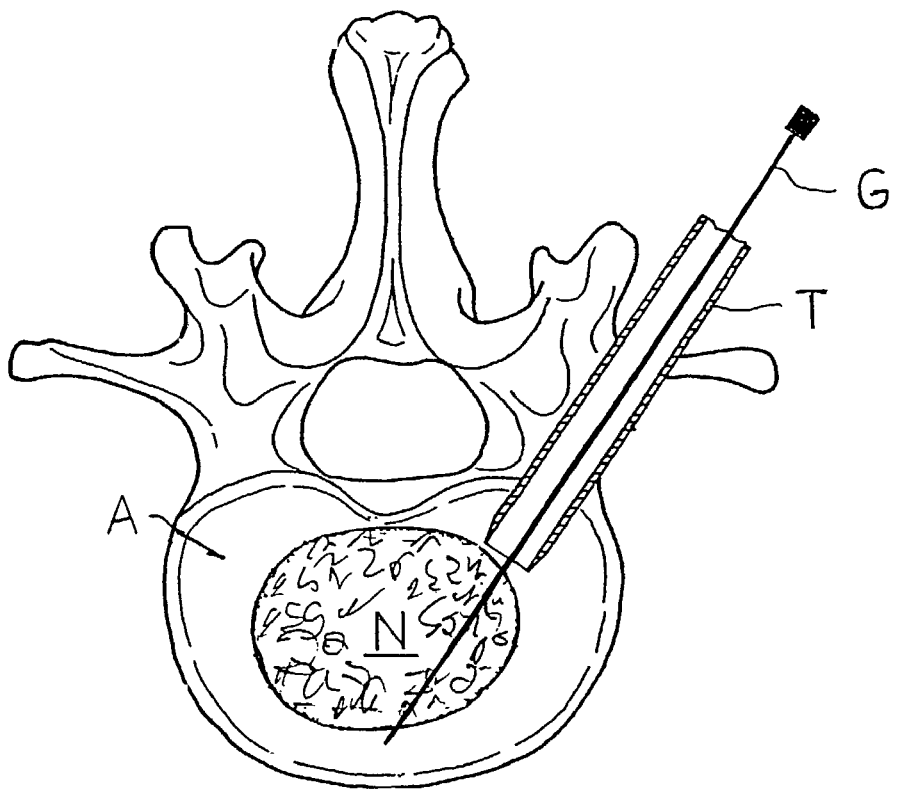
FIG. 3 is a sagittal view of the disc space shown in FIG. 2 with a trephine forming a portal in the annulus fibrosus of the disc.
Figure 4:
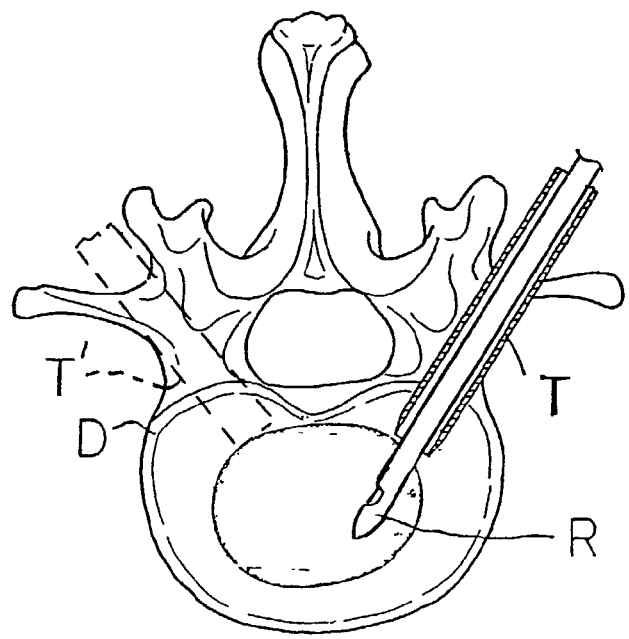
FIG. 4 is a sagittal view of the disc space shown in FIG. 3 with a tissue extraction device positioned within the nucleus pulposus of the disc.

A typical percutaneous discectomy procedure is illustrated in FIGS. 2-4. In the first step, a guide wire G is directed into an affected disc D between two vertebrae, such as the L2 and L3 lumbar vertebrae. As shown in FIG. 2, the guide wire G penetrates the annulus fibrosus A and the nucleus pulposus N, and it preferably anchored at opposite sides of the annulus A. The guide wire G can be positioned and placed under indirect vision, such as fluoroscopy, or stereotactically, or using other known procedures for properly orienting the guide wire within the spinal disc D. The procedure shown in the figures utilizes a posterior approach, which is preferable for implementation of the present invention. Of course, other approaches may be utilized for the discectomy in accordance with known surgical procedures. In addition, the access location may be dictated by the location of a fissure or herniation of the disc.

A trephine T is advanced over the guide wire and driven through the annulus A, thereby forming a portal into the disc nucleus. As shown in FIG. 4, a tissue removal device R can be advanced through the trephine T or through a working channel cannula aligned with the disc portal. The device R can then be used to remove all or part of the nucleus N of the disc D. As depicted in dashed lines in FIG. 4, a second trephine T' can be used to create a second annular portal to facilitate complete removal of the nucleus pulposus of the disc. The tissue removal device R can be of a variety of types, such as a rongeur, tissue morcellator, rotary and/or reciprocating vacuum-assisted cutter, and even a chemical introducer to direct a chemical such as Chymopapain into the nuclear space. Removal of the nucleus leaves a cavity C (see FIG. 5) surrounded by the substantially intact annulus A.

The present invention contemplates the introduction of a biomaterial into the disc cavity C that is capable or restoring disc height and preferably substantially normal disc function. For instance, any of the biomaterials discussed above can fill the newly formed cavity. In accordance with the preferred embodiment, the biomaterial is a fluid with an appropriate flowability and/or viscosity. In particular, the biomaterial must have sufficient flowability to permit relatively easy introduction into the disc cavity C, but with sufficient viscosity to hold its shape within the disc. Since the material being used to fill the disc cavity C is a fluid, the present invention provides means for holding a proper disc height as the material flows into the cavity, to thereby ensure that the cavity is filled—i.e., that the volume of implant biomaterial is the same as the volume of nucleus pulposus removed in the discectomy. Moreover, the methods and devices of the invention provide a means for maintaining the cavity volume as the biomaterial transforms to its solid state.

Prior to the introduction of the above-mentioned biomaterial, the present invention contemplates a process for the pretreatment of the vertebral endplates $E_1$ and $E_2$. The goal of this process is to restore the endplates as closely as possible to their natural state prior to disease or degeneration. The nature of the treatment will depend upon the form of the endplate degeneration and on the type of scaffolding that is intended to be introduced in the nuclear cavity C.

Decalcification of the Vertebral Endplates

Figure 6:
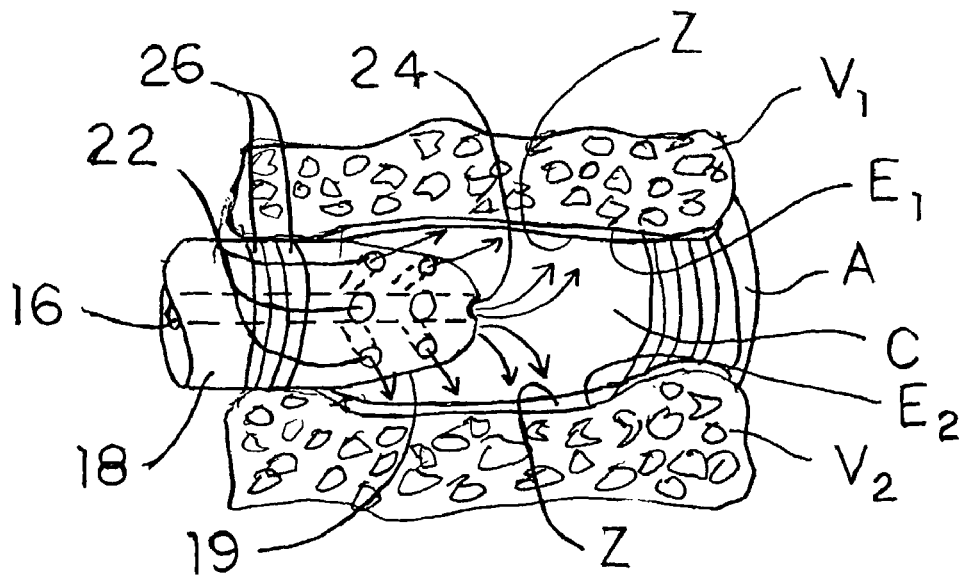
FIG. 6 is a lateral view of the disc space shown in FIGS. 2-5 with the tip of the cannulated distractor of FIG. 5 positioned within the disc space.

Calcification of the articular cartilage of the endplates impedes fluid diffusion across the calcified zone Z, shown in FIG. 6. The endplate contains nourishing channels in the form of vascular buds. Blood vessels extend from the subchondral bone of the vertebral body into the surface of the endplate where they branch into capillaries. With increasing age, cartilaginous endplates mineralize and this calcified cartilage is gradually replaced with bone. In addition, arterioles, capillaries and venules in the bony nutrient spaces and canals adjacent to the disc can become thickened or clogged with proteoglycans, and are often obliterated with carbohydrate containing moieties.

Thus, one treatment in accordance with the present invention is to remove calcifications on the vertebral endplates. Organic compounds are known that are capable of binding calcium and other metals, which can include, but is not limited to, EDTA (ethylenediamine tetra-acetic acid), formic acid, and other dilute acids. When the organic compounds bind to the detrimental metals, the resulting combination can be flushed from the disc space to eliminate the endplate calcification.

Calcification impedes fluid diffusion across the endplates. In addition, it has been found that large proteoglycans, such as aggrecan, can also hinder the passage of certain solutes through the endplates. The removal of these proteoglycans via an appropriate enzyme, such as trypsin, can further enhance the permeability of the endplate. In a typical embodiment, this treatment will accompany treatment for calcification.

Improve Vascularity of the Endplates

Vascularity through the endplate is, of course, critical to proper biological functioning of the disc. Certain health conditions can exacerbate the decrease in vascularity normally associated with aging. For instance, nicotine can cause a reduction in vascular buds and an interruption of the vascular networks in the vicinity of the endplate. Chemical treatments are known that increase vascularity in tissues, such as cytokines and growth factors capable of inducing endothelial cell growth (e.g., VEGF, vascular endothelial growth factor).

The present invention contemplates treatment of the vertebral endplates in this manner If it is determined that the endplates suffer from poor vascularity. In the case of an elderly patient, poor vascularity can be presumed and the treatment administered without separate verification. Alternatively, the status of the vertebral endplates can be verified under direct vision, such as through an endoscope inserted into the nuclear cavity C, or indirectly, such as by way of a CT scan, MRI, PET or comparable scanning technology. This same verification process can be utilized to evaluate the extent of calcification, if any, of the endplates in anticipation of application of a decalcifying agent as described above.

Enhance Integration of Prosthesis/Graft with the Endplates

Systems have been under investigation for some time for the replacement or augmentation of the disc by introducing either a partial or a total nuclear prosthesis. Solid or injectable in situ curable biomaterials require that the prosthesis stay well fixed within the disc space. Anchorage and integration at the graft-host interface (i.e., between the prosthesis and the endplates) is extremely desirable, and in some cases essential to the viability of the prosthesis. However, the cartilaginous endplates and the annulus fibrosus contain abundant large and small proteoglycans that may impede integration between these tissue and the prosthesis.

Clinical researchers have proposed enzymatic digestion of cartilage disruptions to denude it of proteoglycans and allow for interdigitation with the newly synthesized matrix components. It has been found that a protease treated matrix has much less structured water and matrix, and is more easily infiltrated with newly synthesized matrix from repair tissue. More specifically, it is known that trypsin is an enzyme that clips the core protein of aggrecan and other matrix proteoglycans, leaving the collagenous scaffold intact. Pre-treatment of affected endplates with trypsin will allow cartilaginous tissue buds to extend from adjacent tissue into a pre-treated graft to create an undulating, well-integrated surface at the graft-tissue interface.

Hyaluronan is another major component of the cartilaginous endplates, forming the backbone of the large proteoglycan aggrecan. Hyaluronidase is used to digest aggrecan by proteolytic attack of the hyaluronan backbone. It has been demonstrated that a sequential digestion of the cartilaginous matrix with hyaluronidase followed by trypsin effectively extracts proteoglycan without any significant disruption of the underlying collagen fiber network.

Thus, in one aspect of the invention, the affected endplates can be treated with trypsin, or with the sequential application of hyaluronidase and trypsin. Again, as with the treatments mentioned above, the state of the endplates can be first verified before any chemicals are introduced into the nuclear cavity C. Certainly, if the endplates exhibit defects and/or calcification, all of the above treatments, including the treatment to enhance integration, may be indicated. On the other hand, the nature of the graft or prosthesis may militate in favor of pre-treating the endplates, and even the annulus fibrosus, with materials to enhance integration.

Enhance Cell Migration from the Endplate to the Scaffold

Tissue engineering involves the use of systems of cells, scaffolds and growth factors/cytokines to reconstruct and regenerate tissues and organs. Certain disc prostheses may be populated with cells from the patient's own natural disc prior to injection. Cells may also be harvested from other cartilaginous tissues of the body, such as the non-articulating areas of hyaline cartilage in the knee. Adult mesenchymal stem cells may be isolated and purified from bone marrow or adipose tissue.

However, accessing, isolating and purifying cells in this manner can pose a host of problems. One way to avoid these problems, and one way that is well-suited for the present invention, is by implanting an acellular scaffold. In this approach, cells are not actually placed in/on the scaffold, but are instead allowed to migrate into and populate the scaffold. It has been found that the trypsin pre-treatment of cartilage explants allows chondrocytes to proliferate and rapidly replenish matrix lost during the trypsin treatment. Removal of the extracellular matrix induces chondrocytes to resume DNA synthesis and to proliferate.

The present invention contemplates performing one or more of the above treatments to the intervertebral space and vertebral endplates prior to introduction of the prosthetic scaffold, whether a solid implant or a curable fluent biomaterial. It can be noted that some treatments accomplish multiple objectives. For instance, trypsin functions to cleave proteoglycans which increases endplate permeability and enhances cartilage integration with the graft/scaffold. While trypsin affects proteoglycan structure, it does not affect or disturb the structural integrity the collagen-rich outer annulus fibrosus.

In one specific procedure according to the present invention, after completion of the discectomy, the disc space is assessed to determine its condition, and primarily the condition of the vertebral endplates. If it is determined (or assumed) that the endplates are calcified within the nuclear cavity, the disc can be treated with a decalcifying agent such as EDTA or some other dilute acid. The decalcifying agent is maintained in contact with the endplates over a suitable incubation duration, after which the agent, along with the byproducts of its operation, can be flushed from the disc space.

Next, a solution can be introduced to cleave the proteoglycans in the endplates. In a preferred embodiment, that solution is trypsin. In a specific embodiment, the trypsin can be provided in a 0.25%-10% solution with its incubation time a function of the solution strength. For example, a 0.25% solution may require up to six hours, while a 10% solution may only need to operate for ten minutes. Other solution can be used, such as hyaluronidase (e.g., 0.2% for 2 hours, or 4% for 5-10 minutes), or chondroitinase ABC. Once the incubation time has expired, the solution and its byproducts are flushed from the disc space and the cavity is well irrigated, such as with a saline solution.

If vascularity is an issue, various cytokines and/or growth factors can be injected into the nuclear cavity. One preferred material is VEGF. Nominally, the materials in this treatment become absorbed into the endplates so only a minimal incubation time may be necessary, and no flushing would be required after application of the treatment. Besides direct delivery of cytokines, known methods of gene therapy may be used to transfect resident cells (e.g., chondrocytes or endothelial cells) on a transient basis to secrete the cytokine of interest. Since this cell growth stimulating material is intended to remain, this treatment can be reserved to the end of the process, where other treatments require flushing of the material after application.

If it is desired to enhance cartilage integration, the trypsin treatment mentioned above can be utilized. Other components of the extracellular matrix may also be targeted by appropriate materials, such as proteolytic enzymes. A proteolytic inhibitor may be necessary following incubation to de-activate the protease or enzyme. Collagen can be removed using a collagenase. General matrix cleavage can be accomplished with pronase, protease K and papain. In this step, a "cocktail" of various enzymes can be injected and incubated to optimize matrix removal and subsequent integration.

Figure 5:
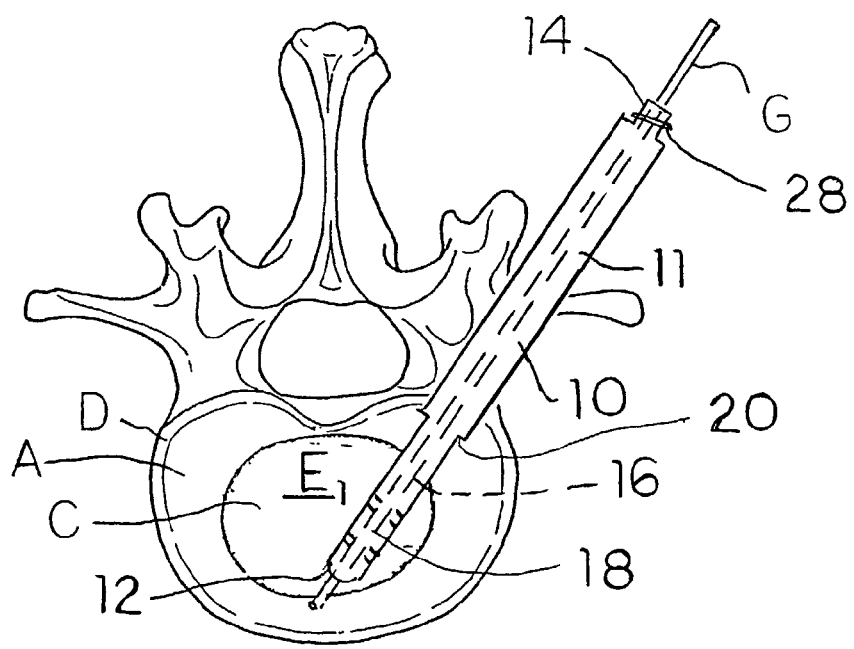
FIG. 5 is a sagittal view of the disc space shown in FIGS. 2-4 with a cannulated distractor in accordance with one embodiment of the present invention.

In accordance with one aspect of the invention, means are provided for introducing the various chemical treatments into the nuclear cavity C, and particularly to direct the treatments to the vertebral endplates. The invention contemplates a cannulated distractor 10 as shown in FIGS. 5-6. In order to ensure that the injectable material reaches the endplates, it is important that the disc space retain its normal height. A certain amount of distraction can be accomplished by positioning of the patient. However, the cannulated distractor ensures that the adjacent vertebrae are properly distracted.

The distractor 10 includes a distal end 12 that extends into the disc cavity C and a proximal end 14 that is configured to engage a device for injecting the fluent material into the disc space. The distractor 10 includes a cannula 11 that terminates in a distraction tip 18 at the distal end of the device. A lumen 16 is defined along the entire length of the device from the proximal end 14 to the and through the distraction tip 18. The distraction tip 18 is sized to extend through the portal formed in the disc annulus A (see FIG. 3). The distractor 10 can include a shoulder 20 proximal to the distraction tip 18, in which the shoulder is sized to prevent passage through the annular portal. The shoulder 20 can operate to limit the distance that the distraction tip 18 extends into the disc cavity C.

As shown in FIG. 6, the distraction tip 18 is intended to be inserted through the annular portal and is configured to restore the appropriate intradiscal height in the cavity C. Thus, in one embodiment, the distraction tip 18 can include a tapered leading portion 19. This leading portion 19 can be introduced into the cavity C and as the tip is advanced further into the cavity the leading portion will gradually distract the adjacent vertebrae as the leading portion 19 bears against the disc endplates $E_1$ and $E_2$. In a specific embodiment, the tapered portion 19 can be substantially bullet-shaped, as shown in FIG. 6. With this configuration, the distraction tip 18 can have any rotational orientation when the tip is inserted through the annular portal. Other forms of distraction tip 18 are contemplated as appropriate for the particular patient anatomy, as well as appropriate for the configuration of the portal formed in the annulus fibrosus.

Referring to FIG. 6, in accordance with one feature of the invention, the distraction tip 18 includes a number of side orifices 22 and an end orifice 24 that all communicate with the central lumen 16. The orifices 22, 24 provide an exit path for fluid injected through the lumen 16. The orifices are oriented to be unobstructed by the vertebral endplates $E_1$ and $E_2$, and most preferably are oriented to direct the fluent material directly onto the endplates.

Since fluid is intended for introduction through the distraction tip 30, it is preferable that some feature be provided to ensure a substantially fluid-tight seal at the entrance to the disc cavity C through the annular portal. Thus, in one embodiment of the invention, the distraction tip 18 can include annular rings 26 that are intended to bear against the disc endplates E and/or the disc annulus A in a sealing relationship. The rings 26 can be integral with the distraction tip 18, or can be separate components mounted on the distraction tip, such as in the form of elastomeric seal rings.

The distractor 10 includes a fitting 28 defined at the proximal end 14 of the cannula 11. The fitting 28 provides means for making a fluid-tight connection with a device adapted to inject the fluent material into the disc. In a specific embodiment, the fitting 28 is a universal fitting, such as a LUER® fitting. This fitting can engage a syringe or another other suitable injector device. In addition, in order to flush the disc cavity C following a particular treatment, the fitting can be adapted to engage a lavage and a suction device. The lavage can include pulsatile filling of the cavity with a neutral fluid, such as saline, and then removal of the fluids by an appropriate suction device. Optimally, the suction device can simply constitute a syringe that can be manually operated to withdraw the minimal amount of fluid within the cavity without risk of generating unhealthy suction pressure.

As explained above, the cannulated distractor 10 of the present invention is utilized after a discectomy procedure. For purposes of illustration, it has been assumed that a total discectomy has been performed in which substantially all of the nucleus pulposus has been removed, leaving a disc cavity C as shown in FIG. 5. If a bilateral approach has been used (as represented by the first and second trephines T and T'), one of the annular portals can be sealed with a material compatible to the disc annulus fibrosus. When the nucleus has been cleared, the guide wire G can be repositioned within the disc D, again preferably using known guidance and positioning instruments and techniques. The cannulated distractor 10 can then be advanced over the guide wire until the distraction tip 18 is properly situated within the nuclear cavity C. Preferably, the proper depth for the distraction tip 18 can be determined by contact of the shoulder 20 with the outer annulus A.

The tapered portion 19 of the distraction tip gradually separates the adjacent vertebral endplates $E_1$ and $E_2$ as the distraction tip 18 is driven further into the disc space. A mallet, impactor or other suitable driver can be used to push the tapered portion 19 into position against the natural tension of the disc annulus. It is understood that the goal of this step is to fully distract the intervertebral space to a proper disc height for the particular spinal level. For instance, for the L2-L3 disc space, the appropriate disc height may be 13-15 mm, so that the distraction tip is positioned within the cavity C to achieve this amount of distraction. As shown in FIG. 5, preferably only one cannulated distractor 10 is utilized, since the distraction tip 18 necessarily occupies a certain portion of the volume of the cavity C. However, a second cannulated distractor and associated distraction tip may be necessary (such as through a second annular portal as shown in FIG. 4) to achieve the proper disc height.

When the distraction tip, such as tip 10, is inserted to its proper depth within the disc cavity C, the annular portal is sealed, whether by contact with the shoulder 20, or by engagement of the rings 26 with the endplates $E_1$ and $E_2$ or the interior of the annular portal. At this point, the fluent treatment material can be injected into the cannulated distractor, and specifically through the lumen 16, once the guide wire G has been removed. The treatment material exits through the orifices 22, 24 in the distraction tip 18 to fill the cavity C. The orifices 30, 32 are preferably positioned and sized to achieve complete and rapid dispersion of the material throughout the cavity.

It should be apparent that the distraction tip 18 maintains the proper disc height while the treatment material is injected. The tip can be retained in position until the injected material has had time to incubate or perform its essential function. Where the incubation time is short, the entire treatment process can occur in a single surgical procedure. However, where the incubation time is lengthy (such as the six hour trypsin incubation time mentioned above), it may be desirable to temporarily close the surgical wound. Since the present invention contemplates introduction of the fluent treatment material through a cannulated distractor, minimally invasive techniques can be utilized, which means the surgical wound is minimal.

Figure 8:
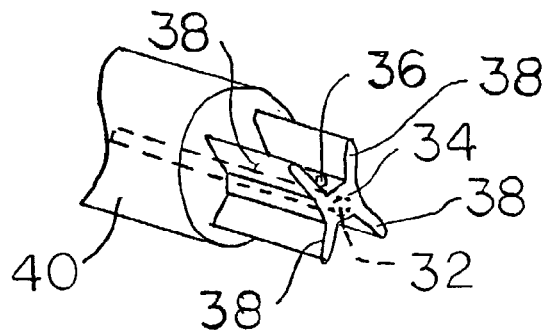
FIG. 8 is a perspective view of the cannulated distractor shown in FIG. 7.

In certain embodiments, the cannulated distractor, such as the distractor 10 shown in FIG. 5, can be left in position. The proximal end 14 can be sealed while the treatment material incubates. Alternatively, the distraction tip 18 can be removable from the cannula 11 so that the cannula can be removed while the tip is kept in its distraction position. Thus, the tip 18 and cannula 11 can be provided with a removable mating element 19, such as a press-fit (as shown in FIG. 8) or a threaded or LUER® type fitting (not shown) as would occur to a person of skill in this art. Once the pre-treatment material has incubated, the distraction tip 18 can be removed, whether the tip is separate or is integral with the cannula 11.

As described above, the cannulated distractor 10 is initially used for the pre-treatment of the disc space in accordance with the present invention. Once the pretreatment has been completed, the cannulated distractor can then be used for the injection of a curable biomaterial of the type described above. Use of the cannulated distractor for this purpose is disclosed in provisional application Ser. No. 60/336,002, entitled "Devices, Methods and Assemblies for Intervertebral Disc Repair and Regeneration", filed on Nov. 1, 2001, and co-pending utility patent application Ser. No. 10/282,755, entitled Devices and Methods for the Restoration of a Spinal Disc, and filed on Oct. 29, 2002 which claims priority to the first mentioned provisional application. The disclosures of both applications are Incorporated herein by reference.

The distractor 10 in the prior illustrated embodiment provides a fluid passageway for dispersing the fluid throughout the entire disc cavity C. In some cases, only a portion of the intervertebral endplate is diseased or damaged and in need of some form of pre-treatment. In that case, it is not desirable to expose healthy endplate or even healthy inner annulus fibrosus to the pre-treatment materials. In an alternative embodiment, shown in FIG. 7, a cruciate distraction tip 30 is depicted. The tip 30 includes a central lumen 32 defined in a central body 34. A number of openings 36 extend from the central lumen 32 to provide a passageway for the pre-treatment fluid material.

Figure 7:
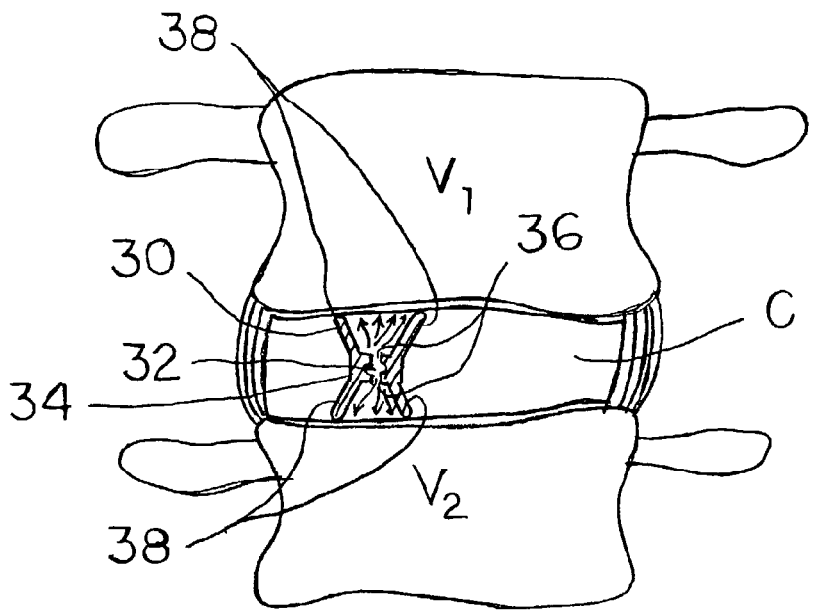
FIG. 7 is an A-P view of a disc space with a cannulated distractor, shown in cross-section, in accordance with a further embodiment of the invention that provides for concentrated treatment of the vertebral endplates.

The cruciate distraction tip 30 includes a number of legs 38 projecting outward from the body 34 and into contact with the vertebral endplates at opposite sides of the disc cavity C. As with the distraction member 10 of the prior embodiment, the cruciate tip 30 is configured to distract the adjacent vertebrae and to hold a proper disc height as the treatment fluid is introduced into the disc space and incubated. However, unlike the prior embodiment, the tip 30 of FIGS. 7, 8 provides means for focused treatment of the endplates. Thus, the legs 38 serve to create an essentially sealed area between the legs and the central body 34. In this way, fluid dispersed from the openings 36 will be exposed to only a specific portion of the vertebral endplates. This approach is especially useful when it is determined that only discrete portions of the endplates are diseased or damaged to a point that requires pre-treatment. The legs 38 then operate as a dam to contain the treatment fluid and prevent the fluid from contacting portions of the endplates that are otherwise acceptable.

In the illustrated embodiment of FIG. 7, the openings 36 provide a fluid path to discrete portions of the opposite endplates. Alternatively, the openings can be concentrated to one side so that the fluid treatment is applied to a portion of only one endplate.

As shown in FIG. 8, the distraction tip 30 can extend from a cannula 40 that can be similar to the cannula 11 described above. The tip can be integrally formed with the cannula, but is preferably detachable. As also shown in FIG. 8, the central lumen 32 terminates in an opening at the end of the tip, since the purpose is to limit the exposure of the pre-treatment material. With the embodiment shown in FIG. 8, it is contemplated that the distraction tip 30 will span the disc space so that the distal end of the tip will bear against the disc annulus opposite the annular portal through which the cannula 40 extends. In this way, the annulus can help seal the end of the channel formed between the legs 38 of the cruciate distraction tip. Alternatively, the distraction tip can be formed with a web at the distal end of the tip, in which the web is co-extensive with the legs to form a fully enclosed volume.

Figure 9:
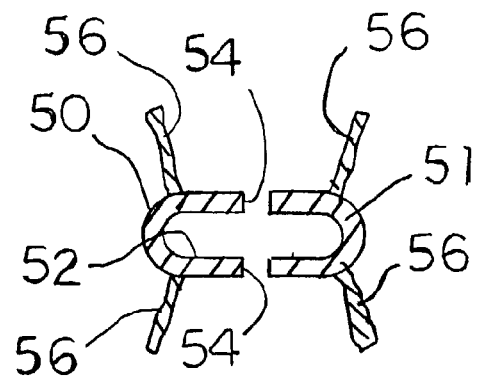
FIG. 9 is an end cross-sectional view of an alternative embodiment of a cannulated distractor similar to the distractor shown in FIGS. 7 and 8.

The same concept of limited pre-treatment of the vertebral endplates can be accomplished by an alternative embodiment shown in FIG. 9. In this embodiment, a dispensing tip 50 includes a central body 51 that is generally tubular. The body is preferably oval in shape, as shown in FIG. 9. The body defines a central lumen 52 that communicates with a number of openings 54. In this embodiment, the dispensing tip 50 includes legs 56 that extend from the body that are in the form of a conformal seal. In this embodiment, the legs 56 do not serve to support the adjacent vertebrae, but are instead operable only to create a sealed volume about a specific region of the vertebral endplates. The legs can therefore be formed of a resilient material, such as a biocompatible polymer, that may be different from the material of the central body 51.

The dispensing tip 50 can be connected to a cannula, as with the previous embodiments, either integrally or by some form of removable attachment. Since the tip 50 is not intended to provide a distraction capability, it can be maintained in position by the cannula.

In accordance with certain embodiments, the cannulated distractors, and particularly the distraction tips, described above can be formed a variety of bio-compatible materials. As explained above the distraction tips must be sufficient strong to maintain proper distraction of the disc space until the biomaterial has been fully injected and cured, if necessary. In certain embodiments, the distraction tips are formed of a bio-compatible metal, such as stainless steel or titanium. In other embodiments, the distraction tips are formed of a polymer or plastic that is preferably radiolucent to permit visualization of the distraction tip in situ to verify the position of the component. In other embodiments, the distraction tip can be formed of a bio-resorbable material.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A method for the treatment of an intervertebral disc prior to the introduction of a disc prosthesis or graft comprising the steps of:
providing a fluent material including a decalcifying agent capable of reacting with the endplate of a vertebra adjacent the disc to decalcify the endplate;
removing at least a portion of the nucleus pulposus of the intervertebral disc to expose at least a portion of the endplate to the disc space; and
injecting the fluent treatment material into a substantially enclosed volume within the disc space so that the fluent treatment material comes into contact and reacts with a portion of the endplate that is less than the entire exposed area of the endplate to prepare the portion of the endplate to accommodate a disc prosthesis or graft subsequently introduced into the disc space.

2. The method for the treatment of an intervertebral disc according to claim 1, further comprising the step of retaining the fluent treatment material within the substantially enclosed volume within the disc space for an incubation period.

3. The method for the treatment of an intervertebral disc according to claim 1, further comprising the subsequent step of flushing the disc space to remove the fluent treatment material and any byproducts of the operation of the fluent treatment material on the portion of the endplate.

4. The method for the treatment of an intervertebral disc according to claim 3, wherein the flushing step includes a lavage and suction of the disc space.

5. The method for the treatment of an intervertebral disc according to claim 1, wherein the step of injecting a fluent treatment material includes simultaneously maintaining the vertebrae adjacent to the disc in a distracted position.

6. The method for the treatment of an intervertebral disc according to claim 5, wherein the step of injecting a fluent treatment material includes introducing a cannulated distractor into the disc, the distractor operable to distract the adjacent vertebrae and including a lumen in communication with the exposed portion of the endplate through which the fluent treatment material is injected.

7. The method for the treatment of an intervertebral disc according to claim 6, further comprising the subsequent step of introducing a fluent biomaterial through the lumen of the cannulated distractor, the fluent biomaterial being curable in situ to form a prosthesis within the disc space.

8. The method for the treatment of the intervertebral disc according to claim 5, wherein the distracted position is the normal anatomic height of the intervertebral disc 9. The method for the treatment of an intervertebral disc according to claim 1, wherein the fluent treatment material is an acid.

10. The method for the treatment of an intervertebral disc according to claim 9, wherein the decalcifying agent is EDTA.

11. The method for the treatment of an intervertebral disc according to claim 1, wherein the step of removing at least a portion of the nucleus pulposus includes performing a discectomy through a portal formed in the annulus fibrosus of the disc.

12. The method for the treatment of an intervertebral disc according to claim 11, the step of injecting the fluent treatment material occurs through the portal formed in the disc annulus.

13. A method for the treatment of an intervertebral disc prior to the introduction of a disc prosthesis or graft comprising the steps of:
providing a fluent treatment material including a decalcifying agent capable of reacting with the endplate of an adjacent vertebra to decalcify the endplate;
removing at least a portion of the nucleus pulposus of the intervertebral disc to expose at least a portion of the endplate to the disc space; and
injecting the fluent treatment material into a substantially enclosed volume within the disc space so that the fluent treatment material comes into contact and reacts with the exposed portion of the endplate to decalcify said exposed portion to accommodate a disc prosthesis or graft subsequently introduced into the disc space.

14. The method for the treatment of an intervertebral disc according to claim 13, further comprising the subsequent step of flushing the disc space to remove the fluent treatment material and any byproducts of the operation of the fluent treatment material on the portion of the endplate.

15. A method for the treatment of an intervertebral disc prior to the introduction of a disc prosthesis or graft comprising the steps of:
providing a fluent material including a decalcifying agent capable of reacting with the endplate of an adjacent vertebra to decalcify the endplate;
removing at least a portion of the nucleus pulposus of the intervertebral disc to expose at least a portion of the endplate to the disc space;
injecting the fluent treatment material into a substantially enclosed volume within the disc space so that the fluent treatment material comes into contact and reacts with the exposed portion of the endplate to prepare said exposed portion to accommodate a disc prosthesis or graft; and
subsequently removing from the disc space substantially all of the fluent material prior to introduction of the disc prosthesis or graft into the disc space.

16. A method for the treatment of an intervertebral disc comprising the steps of:
providing a fluent material including a decalcifying agent capable of reacting with the endplate of an adjacent vertebra to decalcify the endplate;
removing at least a portion of the nucleus pulposus of the intervertebral disc to expose at least a portion of the endplate to the disc space;
injecting the fluent treatment material into a substantially enclosed volume within the disc space so that the fluent treatment material comes into contact and reacts with the exposed portion of the endplate to prepare said exposed portion to accommodate a disc prosthesis or graft; and
providing a disc prosthesis or graft into the disc space separate from the fluent treatment material.

* * * * *